United States Patent [19]

Binder

[11] 4,207,892

[45] Jun. 17, 1980

[54] METHOD AND APPARATUS FOR THE DIAGNOSIS OF TISSUE SAMPLES

[76] Inventor: Arnold Binder, Bernhardstrasse 21, 8750 Aschaffenburg, Fed. Rep. of Germany

[21] Appl. No.: 935,880

[22] Filed: Aug. 23, 1978

[30] Foreign Application Priority Data

Sep. 13, 1977 [DE] Fed. Rep. of Germany ....... 2741068

[51] Int. Cl.² .............................................. A61B 6/00
[52] U.S. Cl. ................................... 128/665; 356/340; 250/373
[58] Field of Search ...................... 128/665, 2 A, 2 R; 356/51, 337, 432, 244, 340, 338; 250/272, 372, 373

[56] References Cited

U.S. PATENT DOCUMENTS

| | | | |
|---|---|---|---|
| 3,327,119 | 6/1967 | Kamentsky | 128/2 A |
| 3,342,099 | 9/1967 | Kaye | 356/340 |
| 3,826,920 | 7/1974 | Woodroffe et al. | 250/373 |

*Primary Examiner*—Willis Little
*Attorney, Agent, or Firm*—Toren, McGeady and Stanger

[57] ABSTRACT

A diagnostic technique to histologically detect malignancy and other tissue properties is performed by pressing a solid tissue sample between a pair of planar parallel plates transparent to ultraviolet light to a fraction of the original thickness of the sample and by subsequently passing focused ultraviolet light therethrough. The ultraviolet light is passed transversely to the planar glass plates and the emerging angularly distributed light is analyzed to determine a dignity parameter of the sample containing diagnostic information. The dignity parameter is a unique, monotonous and continuous function of the relation of the forward scatter coefficient to the extinction coefficient of the compact portions of the tissue of the sample.

13 Claims, 2 Drawing Figures

METHOD AND APPARATUS FOR THE DIAGNOSIS OF TISSUE SAMPLES

The invention relates to a method for the diagnosis of tissue samples, and more particularly to a method enabling relatively quick diagnosis of tumors. The invention includes an apparatus for performing the method.

In the classical histology the "condition" of tissue is judged on the basis of the microscopic impression of the tissue. The judgment criteria applied are usually the architecture and type of growth of the tissue, but statements regarding the characteristics of the tissue cells may also be included. Aside from the classical histology, cytology has reached significance in recognizing tumors. In this case, a diagnosis is made solely on the basis of changes in individual tissue cells. However, classical cytology (Papanicolaou) which also involves utilization of the microscope, does not yield the extensive results afforded by the histology of the tissue.

In the application of classical histology as well as with cytology, there is required a relatively long time for preparation and highly qualified personnel are needed for making a reliable diagnosis. The setting up of a prior art histological preparation includes staining and embedding the tissue in a support material (paraffin) and making thin cuts for a microscopic observation. The cytological preparation includes the making of a smear and the fixation and staining of the cell material.

Since pathologists, histologists and diagnosticians using cytology will find themselves heavily overburdened due to the multitude of the samples which must be tested, significant effort has been directed toward providing methods which are of a more automatically operating nature and which will produce a quicker diagnosis.

In this regard, a number of techniques have been developed which are intended to eliminate or at least reduce the need for microscopic observations. These techniques are described hereinafter.

Procedure a

The ion content of the tissue cells is examined. For this purpose the cell material is evaporated by means of laser or electron beams. The portion of certain types of ions can then be determined in the vapor by means of spectroscopy or mass spectroscopy. The diagnostic safety of the method is high; however, it is only possible to distinguish between benign and malignant. It is not possible to differentiate more finely. The method is too complicated and too sensitive for clinical use. For example, the slightest presence of impurities of the sample holder falsifies the diagnosis.

Procedure b

A morphological parameter of the tissue cells is determined (for example the nucleus-plasma relation). This is done by means of coherent optical methods. the cells must be suspended in a liquid. This means in the case of a solid tissue sample that a cell suspension must be made by a cumbersome preparation method. Preparation damages can occur in this method. It is also only possible to distinguish between benign and malignant, and even the diagnostic reliability is not high since only a cell parameter is evaluated.

Procedure c

Malignant tissue is determined by means of electron spin resonance measurements. It is not necessary to specially prepare the tissue. However, the diagnostic reliability of the method is slow. On the other hand, an examination can be effected without requiring removal of tissue from the patient. This method is not considered competitive with classical histology or cytology, and it can at most supplement X-ray diagnosis.

Procedure d

With a fast photomoter a certain chemical cell component (for example DNS) is measured. In order to perform this procedure, known as impulse cytophotometry, the cells must be available in an aqueous suspension. Thus, when only a solid tissue sample is available, a complicated preparation for making the suspension must be performed. In addition, since marking of the cell component to be measured is necessary, the cells must be stained. This requires a cumbersome preparation which is susceptible to the danger of mistakes. Indeed, differing opinions can be found in the literature regarding the diagnostic reliability of this method.

Procedure e

A certain chemical cell component (for example DNS) and additionally a morphological cell parameter (cell volume) are determined. As a rule, this is done by means of scattered light and fluorescent light measurement. In this case the cells must also be available in an aqueous suspension. This requires the same type of cumbersome preparation as in Procedure d involving separation of the cells in the case of a solid sample and staining. Although this method involves the danger of mistakes during preparation, the diagnostic reliability is higher than in Procedures b and d.

With the exception of Procedure c, the known methods described above are only partially capable of easing the burden on the pathologist, histologist and cytologist. However, because they are all complicated and because the preparation of the cells is cumbersome, they are not acceptable for performance of a diagnosis during a surgical procedure. In the operating theater, solid tissue samples are usually obtained. Also, the methods described do not enable fine differentiation in the diagnosis of tumors.

The invention is directed toward enabling a diagnostic procedure which avoids the disadvantages of known methods, which particularly does not require the preparation of cell suspensions or the preparation of thin cuts, and which does not require a cumbersome preparation procedure thereby avoiding the danger of mistakes during such a procedure. The method of the invention offers the advantage of high diagnostic reliability and it is one which can be performed quickly and automatically thereby making it particularly suitable for use in the laboratory as well as in the operating theater.

SUMMARY OF THE INVENTION

According to the present invention, a diagnostic procedure is performed by placing a sabil tissue sample between two small planar parallel glass plates and then pressing the sample to a fraction of its original thickness, the thickness of the pressed sample being substantially greater than the thickness of a single cell of the tissue sample. Focused ultraviolet light is then passed through the pressed sample in a direction transversely to the planar sides of the glass plates. The angularly distributed ultraviolet radiation emerging from the sample is then analyzed for determining a dignity parameter which contains the diagnostic information, the dignity parameter being a unique, monotonous and continuous function of the relation of forward scatter coefficient to extinction coefficient of the compact tissue portion of the sample.

The term "sabil tissue sample" as used herein is intended to mean a tissue sample whose thickness is not measured in fractions of millimeters as in known thin cuts. Such samples are immediately obtained, for example, in punch biopsy or in operations. The thickness can be freely chosen with certain limits. For performing the method it is advantageous to use an unprepared tissue layer of approximately one millimeter thickness as the tissue sample.

The method of the invention is intended as suitable not only for use in the laboratory but also in the operating theater. The technique of the invention is considered to be of high diagnostic diversity, and capable of use with a high diagnostic reliability. It allows quick statements regarding the dignity of the tissue, i.e. it distinguishes between benign and malignant. In malignant tumors, the invention enables a determination of the degree of malignancy (histological grading) and it enables diagnosis of inflammatory changes in benign tissue. Important advantages of the method reside in its quickness of performance and in its unproblematic use. When the apparatus is designed appropriately, a diagnosis may be available within only approximately a tenth of a second. The tissue sample is inserted into the apparatus without any preparation. Time-consuming tissue preparations currently in use involving staining, embedding and making thin cuts, are eliminated. Accordingly, the method can also be carried out by a medical-technical assistant. Therefore, the method can be routinely used in laboratory tests as well as for tissue diagnosis during a surgical operation.

For evaluation by measuring techniques it is advantageous to press the tissue sample between the glass plates or object slide to at least approximately one-third of its original thickness.

It was found that ultraviolet light having a wave length $\lambda = 366$ nm is particularly suitable for performance of the method.

From the ultraviolet radiation emerging from the tissue sample, fluorescent light is preferably filtered out in order to eliminate problems in determining the dignity parameter D.

The magnitude of the dignity parameter D indicates whether a malignant or a benign tumor exists, and it indicates the degree of malignancy. It also points out inflammatory changes in benign tissue. Obviously there will exist a clear relationship between D and the clinical and histological diagnosis.

The forward scatter coefficient is determined by the average volume of the cell nuclei of the sample tissue; the extinction coefficient being determined by the average content of nucleic acid of the cells. This is true for compact tissue portions. Accordingly, the relation of forward scatter coefficient to extinction coefficient in compact tissue is linked to the average relation of cell nucleus volume to nucleic acid content of each cell. As can be gathered from publications such as, for example, DKFZ Heidelberg 1970, 1971, the average relation of cell nucleus volume to nucleic acid contents per cell is characteristic for the distinction between benign and malignant samples and it allows statements regarding the degree of malignancy. The dignity parameter D determined by the invention has the same diagnostic validity. In addition, measurements have surprisingly shown that the parameter D also indicates inflammatory changes in the examined tissue.

The method can be carried out in a simple manner by goniometrically measuring the angular distribution of the ultraviolet radiation emerging from the tissue sample, by scanning with an ultraviolet detector, by transmitting its signals to a time-interval integrating digital voltmeter and by evaluating the measured values obtained at the digital voltmeter by means of a computer.

The advantageous measuring techniques of the method of the invention result from the fact that a thick tissue sample is used. This capability permits the quick diagnosis. In the thick sample, damaged cells (for example with cut-open cell nuclei) occur only at the surface of the sample. The number of these damaged cells is negligible and small compared to the number of undamaged cells in the interior of the sample. Accordingly, the major portion of the cells contributing to the measurement is undamaged. The measurement is extremely exact. In the case of conventional scanning technique using histological thin cuts, damaged cells are separated by the examining pathologist. This is time-consuming and laborious.

The apparatus particularly suited for performance of the invention comprises elements arranged on an optic axis with fixed distances therebetween, these elements including an ultraviolet light source, a monochromator, a convergent lens projecting the emerging slit of the monochromator onto the sample, a pair of glass plates carrying the pressed sample, possibly a fluorescent light filter, a goniometer whose center coincides with the sample, an ultraviolet light detector mounted on the movable graduated circle of the goniometer, a time-interval integrating digital voltmeter receiving the measurement signals of the detector, and a computer connected to the digital voltmeter.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there is illustrated and described a preferred embodiment of the invention.

DETAILED DESCRIPTION OF THE PREFERRED EMBODIMENT

Figure 1:
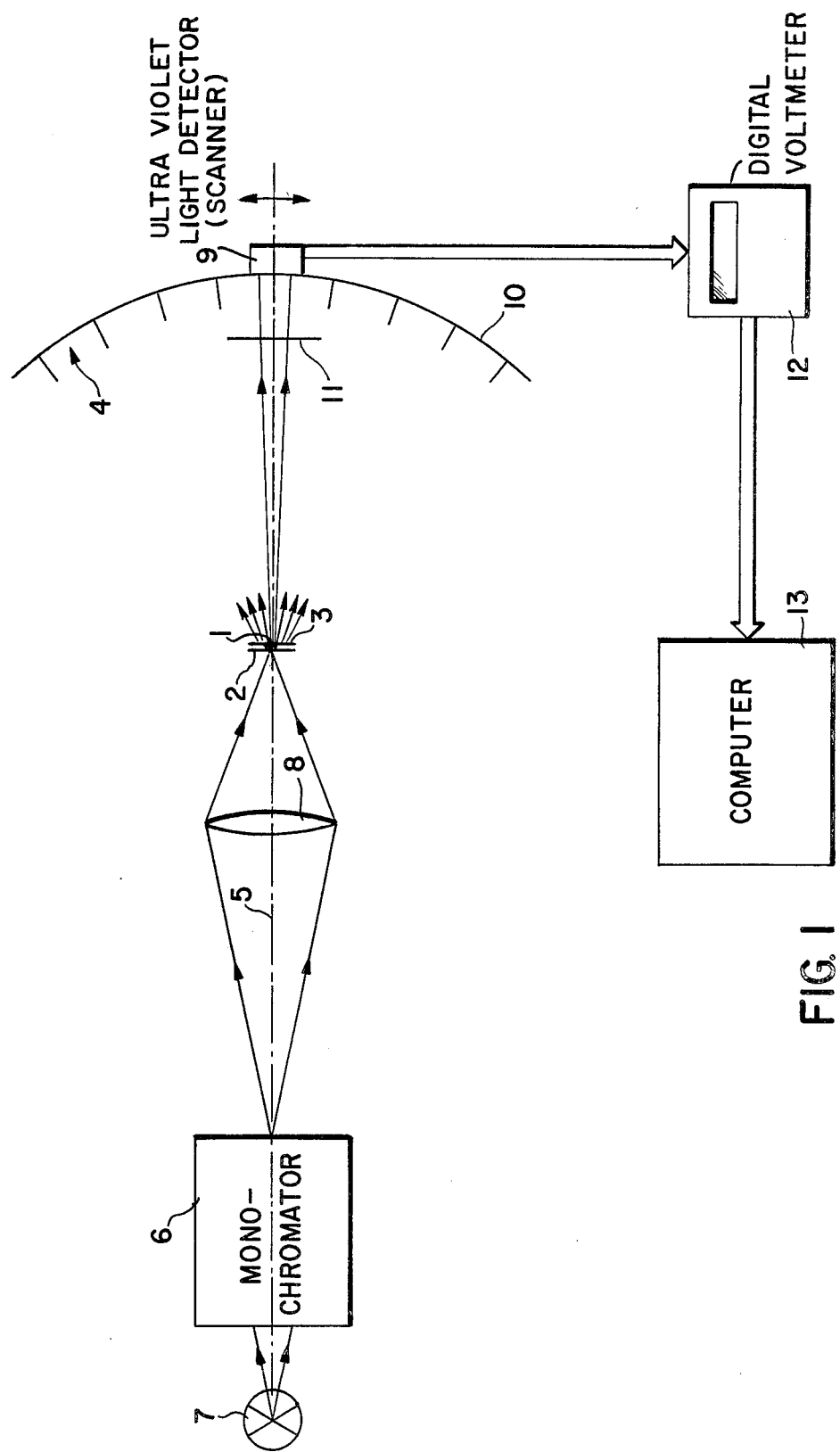
FIG. 1 is a schematic representation of a test setup of the apparatus of the invention.

In FIG. 1 there is shown a sabil tissue sample comprising a tissue layer 1 with a thickness of about 1 mm. In unpressed condition the side of the tissue layer is about $3 \times 6$ mm². The sample tissue is pressed between two object slides 2 and 3, composed of glass having a thickness of about 1.5 mm. The slides 2, 3 are pressed together until the tissue thickness is reduced to about 0.3 mm. The tissue sample utilized with the present invention will have a thickness in excess of the thickness of a single cell of the sample and will be typically pressed between the plates or slides 2, 3 to a thickness substantially in excess of the thickness of a single cell of the sample. The sandwich assembly obtained in this manner is mounted in the center of a goniometer 4 and is illuminated with ultraviolet radiation having a wavelength $\lambda = 366$ nm. The parallel object slides 2, 3 are arranged perpendicularly relative to an optical axis 5 of a light beam impinging the sample from a monochromator 6.

The ultraviolet light source may be a super-pressure mercury lamp 7 (HBO 200W/2) available from the Osram Company with a regulated power supply. The tissue sample 1 is illuminated by means of a lens 8 (focal distance 10 cm, diameter 4 cm) which projects the exit slit of the monochromator 6 (Zeiss MM 12) onto the sample. The radiation spot on the sample has a size of $2 \times 0.4$ mm$^2$. The distance between lens and exit slit of the monochromator is about 70 cm, and the distance between lens and sample is about 11 cm.

An ultraviolet light detector 9 is mounted on the movable graduated circle 10 of the goniometer 4 and scans the angular distribution of the ultraviolet radiation emerging from the sample. The ultraviolet light detector 9 is a semiconductor detector with a circular reception surface whose diameter is 3 cm. The distance between the sample and the detector is about 17.5 cm.

A filter 11 (Schott UG1, 1 mm) mounted in front of the detector 9 prevents strong fluorescent light which emerges from the sample from reaching the detector. Measurements without this filter have also been performed. However, it was found that with the filter a larger change in the significant parameter D occurred. Therefore, all measurements were performed with the filter and only a few without.

From the detector 9 the signals are fed to a digital voltmeter 12. The digital voltmeter 12 integrates over 0.8 seconds. The detector practically operates on open circuit or at no-load and delivers signals at the low measuring voltages which signals are, with sufficient accuracy, proportional to the incoming radiation current when the effect of darkness of the detector is subtracted. The measured values obtained at the digital voltmeter 12 are evaluated by means of a computer 13. The measurements are performed in a dark room so that the detector is only exposed to radiation which emerges from the sample.

When adjusting the goniometer, if the detector 9 is at 0°, the extension of the optic axis 5 of the light beam which falls from the monochromator 6 onto the sample 1 extends through the center of the reception surface of the detector. To determine whether this adjustment is correct, the signals which are corrected for the effect of darkness are determined at two positions which are symmetrical relative to 0°. When the adjustment is correct, these signals are equal.

The evaluation by computation of the measuring signals and the determination of the dignity parameter D are described in detail hereinafter.

For the evaluation by computation, first of all the signals obtained at the digital voltmeter 12 are corrected. First, for each signal the effect of darkness is taken into consideration; this effect of darkness is a voltage which occurs at the detector system even if the detector 9 is not charged with a voltage to be measured. The signal J corrected for the effect of darkness is then proportional to the incoming radiation current. J is converted to the value I which is proportional to the radiation density and which occurs at the detector side of the tissue surface by means of the following formula:

$$I = J \cdot G(\theta a) / \cos \theta i$$

For this correction the refractive indices of tissue and glass are assumed to be equal. The refractive index of the glass of the object slide is $n = 1.5$. Due to the refraction at the surface of the object slide, a light beam which enters at an angle $\theta a$ at the detector 9, leaves the tissue at an angle $\theta i \cdot G(\theta a)$ corrects the refraction and the reflection at the glass surface. Numerical values for $G(\theta a)$ and $\cos \theta i$ are stated in the following table.

The tissue layer, i.e. the sample 1, is to be pressed between the object slides 2, 3 to approximately one-third of its original thickness. In the test setup according to FIG. 1 the object slides are held at a space of approximately 0.3 mm by means of spacers (not shown). This means that the tissue layers to be measured must have a thickness of more than 0.9 mm when they are in the unpressed state. When the thickness of the unpressed tissue becomes significantly larger than 1 mm, the available useful signals at the detector can become weak and the load at the glass due to pressure can become so high that the glass breaks. Therefore, the thickness of the tissue sample 1 is always chosen at approximately 1 mm. The low loading capacity of the glass prevents destruction of the tissue due to too high pressure. In addition, a tissue thickness of more than 0.9 mm ensures that the "thick sample" characteristic for the inventive method is used. Aside from this effect which is important for the evaluation, the pressure between the object slides 2, 3 provides for uniform surfaces of the tissue samples which is important for a defined measurement. Further on the size of the tissue layer in unpressed condition should be approximately the same for all measurements.

So far a simple test setup has been described. For a more practical application of the method an arrangement may be advantageously selected wherein the goniometer 4 and the detector 9 are replaced, for example, by a system of detectors arranged in a circle around the sample 1 as shown in FIG. 5. In this case, the signals of the individual detectors can be made available simultaneously at the evaluating computer thereby making it possible to perform evaluation by computation within a tenth of the second.

| $\theta_a$ | $\cos \theta_i$ | $G(\theta_a)$ |
|---|---|---|
| 0° | 1 | 2.34375 |
| 5° | 0.998310 | 2.34873 |
| 10° | 0.993277 | 2.36394 |

These values are sufficient for the evaluation of the measurement. The values I are subsequently converted to an infinitely small detector. A significant correction only results for 0°. In the following equation, the uncorrected value is indicated by $I_o$, the corrected value by $I_1$.

$$I_1 = I_o (1 + a)$$

wherein $$a = 1 - \frac{(1-v)}{i \cdot \epsilon} \ln\left[1 + \frac{v \cdot \epsilon}{(1-v)}\right]$$

$$\epsilon = 0.0038053$$

$$v = \frac{(J_1/J_2) - 1}{(J_1/J_2) - 0.996195}$$

$J_1$ is the value of the signal corrected for the effect of darkness at the detector at 0°, $J_2$ at $\theta a = 5°$. The meanings of other symbols in the above formulas are:
a = Correction factor of the radiation density
v = Characteristic value of the radiation distribution
$\epsilon$ = Geometry factor of the receiver.

I is not corrected for 5° and 10°.

The digitary parameter D is computed from the corrected I. The corrected I-value for 0° is $I_1$, for $\theta a = 5°$ it is $I_2$ and for $\Gamma a = 10°$ it is $I_3$. The following equations apply:

$$y_1 = \frac{(I_1/I_2) - 1}{(I_1/I_2) - 0.998310}$$

$$y_2 = \frac{(I_1/I_3) - 1}{(I_1/I_3) - 0.993277}$$

$$D = \frac{y_1 + y_2}{2}$$

The pressing of the tissue is important for the determination of D. Due to this pressing, disturbances of the compact tissue, for example glandular ducts, become noticeable only at larger angles of the radiation emerging in the transmission. For angles $\theta a$ of 0° to approximately 15° the angular distribution of the compact tissue applies. In the manner indicated above, by means of measuring values within this angular region the dignity parameter D can be computed according to the "radiative-transfer theory" for compact tissues. In this case, it is assumed that it is a tissue whose consistency may vary to a certain extent from place to place.

The determination of D for the compact tissue portions is important because only in this case is D clearly correlated to the significant cell parameters described in the introduction. The stated evaluation applies for tissue samples beyond a certain thickness. In these samples, the angular distribution of the emerging radiation no longer changes with increasing thickness, i.e. $I_1/I_2$ and $I_1/I_3$ no longer change.

Figure 2:
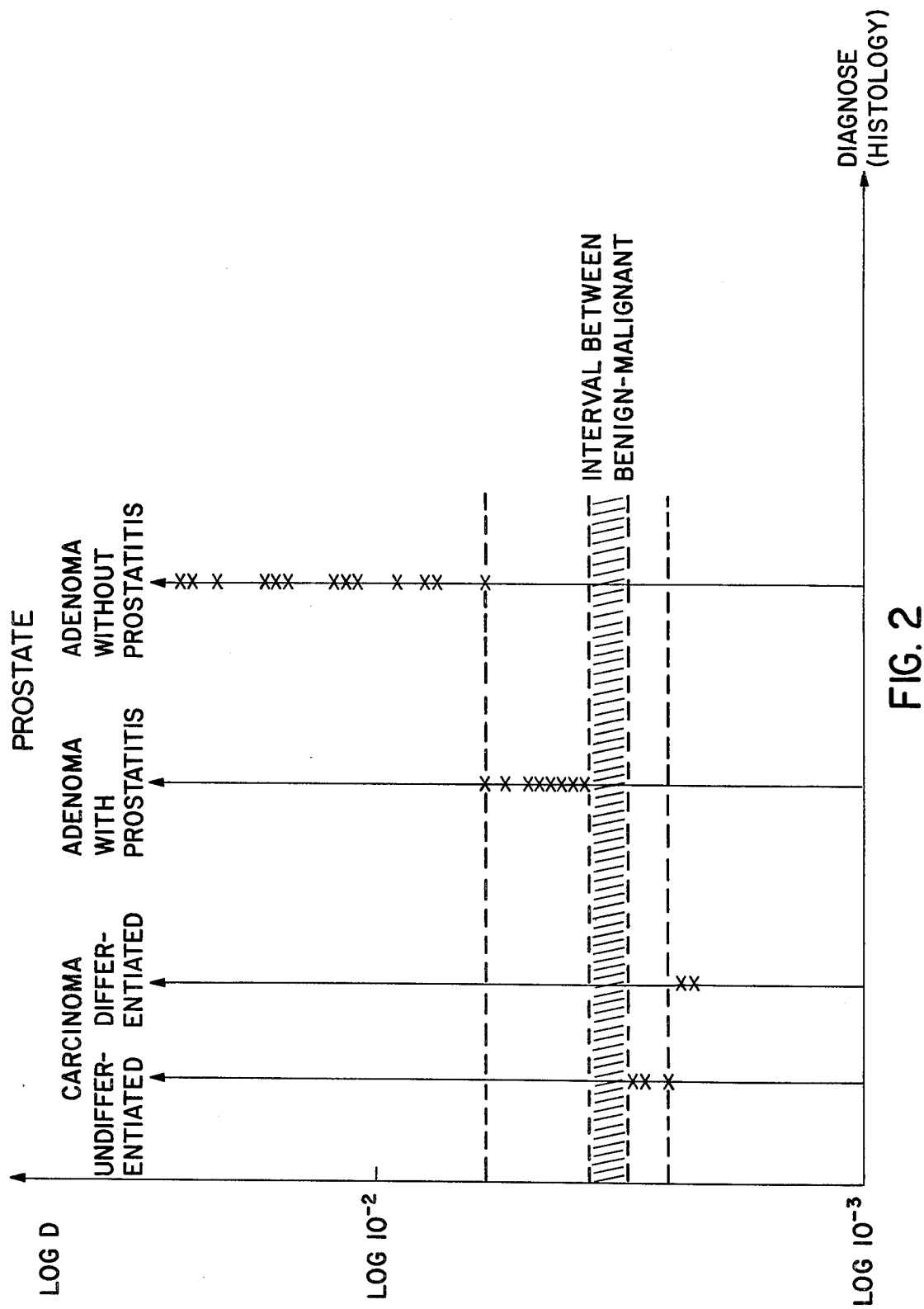
FIG. 2 is a representation of the measured results of a prostate tissue depicted in a system of coordinates.
Figure 3:
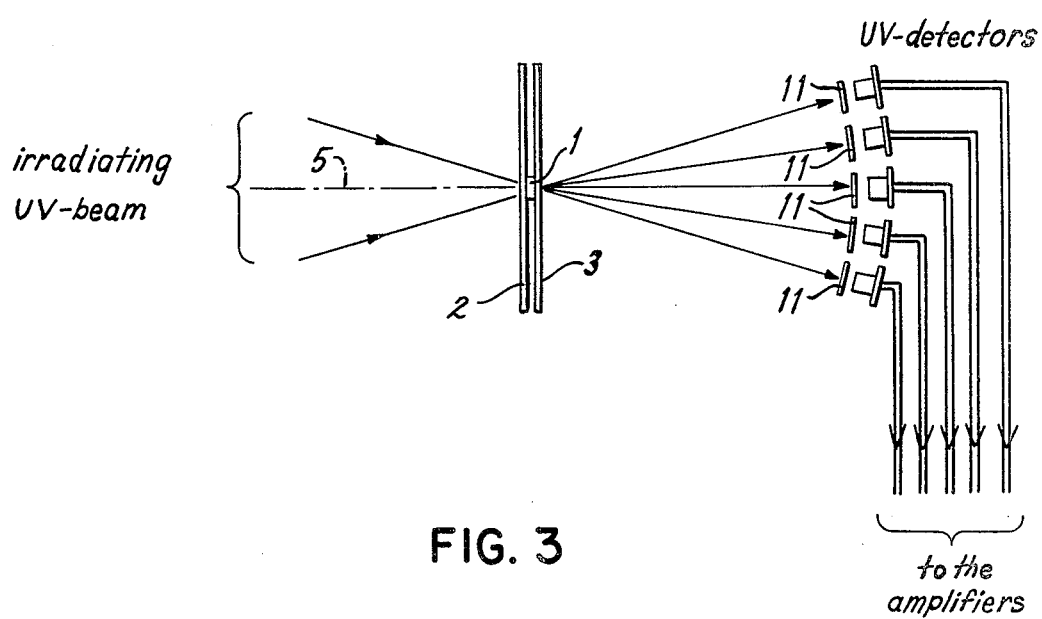
FIG. 3 shows a set-up wherein a plurality of fixed u-v detectors are arranged about a test sample.

An explanation of the use of the method will now refer to FIG. 2. The diagnostic evidence of D for tissue from the human urogenital region has been checked by means of the above-described test setup. The major portions of the sample were measured as blank test samples, i.e. the histological findings were not known. These samples were made available by the Urological University Clinic in Mainz. The check tests were also performed by this Clinic. The samples were made available fixed with Formalin (4% Formalin). A short time after being pressed between the object slides 2, 3, stable signals at the detector 9 were obtained which were suited for the determination of D. The measurements were carried out with the filter UG1 in front of the detector.

The result of a series of measurements of prostate tissue is plotted on the ordinate as the logarithm to the base 10 of the dignity parameter D. Discrete values of the abscissa are assigned to the diagnostic findings are made available by histology. Only preparations were used where histological and clinical findings were in agreement.

The graph shows a clear correlation between the histological finding and the dignity parameter D. In the carcinoma the differentiation of the tumor is indicated. In the benign tumor (adenoma) it is distinguished between inflammatory change (Prostatitis) and free of inflammation. It is also remarkable that in the border regions of carcinoma usually highly inflamed tissue was found, which also was in agreement with clinical experience. The gap or interval between benign and malignant areas seems noteworthy. This suggests the conclusion that there exists a step process in a malignant change. This results from plotting values from the center of the tumor. Fifty-two measurements were used for the graph; the entered crosses correspond to values of D determined by means of the measurements. Not all of these fifty-two D-values are visible, since several of the crosses are superimposed.

A similar picture as in the prostate was developed with regard to the kidney. Maligant tumors were found to produce lower D-values while benign tissue produced higher D-values. However, in contrast to the prostate, areas of inflamed tissues and areas of tissue free of inflammation were reversed. The absolute D-values were also found in a different area than in the prostate. This is in agreement with the histological experience wherein the same tissue picture in one organ can be considered benign, but in another organ it can already be considered as malignant.

Compared to the prostate and the kidney, the effect developed in the bladder is reversed. Malignant tumors correspond to high D-values; benign tumors to low D-values. For surface or top-layer epithelium in experiments with animals such an effect was already found in 1971 at the DKFZ Heidelberg. In Heidelberg, at the time, histological preparations (thin cuts) were scanned with a cytophotometer, and it was possible to eliminate cut-open cell nuclei by means of microscopic observation by the examining pathologist during the measurement. Compared to the quick-diagnosis approach of the invention, this is a time-consuming method which moreover requires highly qualified personnel.

In summary it can be observed that the quick-diagnosis method proposed herein obviously offers a relatively high diagnostic reliability. In the examinations performed to date which were limited to the urogenital region it was always possible to find a clear relation between the values of D and the clinical-pathological findings. Compared to the classical histology, the inventive quick-diagnosis method offers the advantage that it delivers reproducible quanititative results.

The method on which the invention is based must be considered a histological examination method since solid tissue samples are measured. It is less suited for the cytological diagnosis. In the cytological diagnosis it would probably lose its high diagnostic reliability because of the number of available cells. In the solid sample several hundred thousand cells are present in the radiation spot of the ultraviolet measuring radiation.

With the exception of Procedure c, none of the known quick-diagnosis methods described in the introduction delivers a measuring rate of several hundred thousand cells in approximately a tenth of a second as is made possible by the inventive method. However, the known method c has a low diagnostic reliability. Aside from Procedures a and c, the known methods are cytological diagnosis methods, contrary to the method of the invention.

Finally, it should be noted that instead of the monochromator 6 mentioned in the foregoing description of a test setup, a suitable filter can also be used.

While a specific embodiment of the invention has been shown and described in detail to illustrate the application of the inventive principles, it will be understood that the invention may be embodied otherwise without departing from such principles. 9n

What is claimed is:

1. Apparatus for the histological diagnosis of tissue samples, utilizing solid tissues samples particularly for effecting a quick diagnosis of tumors, comprising:
    a pair of planar plates transparent to ultraviolet light for pressing therebetween a solid tissue sample to be diagnosed;
    a source of ultraviolet light arranged to direct said light through said tissue sample pressed between said glass plates;
    convergent lens means located between said tissue sample and said light source;
    monochromator means having an exit slit projected onto said sample by said lens means;
    goniometer means having a movable graduated circle and defining a center located in said sample;
    ultraviolet light detector means mounted on said movable graduated circle of said goniometer means arranged to receive ultraviolet radiation emerging from said tissue sample;
    time-interval integrating digital voltmeter means receiving measuring signals from said detector; and
    computer means connected to said digital voltmeter means;
    said apparatus operating to analyze ultraviolet radiation emerging from said sample to determine a diagnostic parameter of said sample.

2. Apparatus according to claim 1 wherein said ultraviolet light source, said monochromator means, said lens means, said glass plates, said goniometer means and said ultraviolet light detector means are arranged in an optic axis defined by said lens means and spaced a fixed distance apart.

3. Apparatus according to claim 1 further including fluorescent light filter means located between said pair of plates and said ultraviolet light detector means.

4. Apparatus according to claim 1, wherein said ultraviolet light source is a super pressure mercury lamp with a regulated power supply.

5. Apparatus according to claim 1 wherein the spacing and the plane parallelism of said glass plates are fixed by means of spacers.

6. A method for the histological diagnosis of tissue samples, particularly for effecting quick diagnosis of tumors, comprising the steps of: placing a solid tissue sample between a pair of planar members transparent to ultraviolet light; pressing said sample between said members to a thickness substantially greater than the thickness of a single cell of said sample; passing focused ultraviolet light through the pressed sample in a direction transversely to said planar members; analyzing the angular distribution of ultraviolet radiation emerging from said sample; and determining a diagnostic parameter of said sample from said analysis of said angular distribution of said emerging ultraviolet radiation.

7. A method according to claim 6 wherein said diagnostic parameter is a dignity parameter which contains diagnostic information of said sample, said dignity parameter being a unique, monotonous and continuous function of the relation of forward scatter coefficient to the extinction coefficient of the compact portions of the tissue of the sample.

8. The method according to claim 6, wherein an unprepared tissue layer of approximately 1 mm thickness is used as the tissue sample.

9. The method according to claims 6 or 2, wherein said tissue sample is pressed between said glass plates to about a third of its original thickness.

10. The method according to claim 6 wherein the ultraviolet light passed through said tissue sample has a wavelength $\lambda = 366$nm.

11. The method according to claim 1 wherein fluorescent light is filtered out from the ultraviolet radiation emerging from said sample.

12. The method according to claims, 6, 10, or 11 wherein the angular distribution of the ultraviolet radiation emerging from said tissue sample is measured goniometrically and is scanned by means of an ultraviolet light detector whose signals are fed to a time-interval integrating digital voltmeter and wherein the measured values obtained at said digital voltmeter are evaluated by means of a computer.

13. The method according to claims 6, 10, or 11, wherein the ultraviolet radiation emerging from said tissue sample is projected onto ultraviolet light detectors arranged around said sample and wherein the signals of the individual detectors are simultaneously evaluated by computations.

* * * * *